United States Patent
Govari

(10) Patent No.: US 11,832,951 B2
(45) Date of Patent: Dec. 5, 2023

(54) HANDLING ECTOPIC BEATS IN ELECTRO-ANATOMICAL MAPPING OF THE HEART

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/889,419

(22) Filed: Aug. 17, 2022

(65) Prior Publication Data

US 2022/0386931 A1   Dec. 8, 2022

Related U.S. Application Data

(63) Continuation of application No. 16/724,706, filed on Dec. 23, 2019, now Pat. No. 11,490,850.

(51) Int. Cl.
| | | |
|---|---|---|
| *A61B 5/364* | (2021.01) | |
| *A61B 5/35* | (2021.01) | |
| *A61B 5/352* | (2021.01) | |
| *A61B 5/287* | (2021.01) | |
| *A61B 5/06* | (2006.01) | |

(52) U.S. Cl.
CPC .............. *A61B 5/364* (2021.01); *A61B 5/062* (2013.01); *A61B 5/287* (2021.01); *A61B 5/35* (2021.01); *A61B 5/352* (2021.01)

(58) Field of Classification Search
CPC ......... A61B 5/364; A61B 5/062; A61B 5/287; A61B 5/35; A61B 5/352
See application file for complete search history.

(56) References Cited

U.S. PATENT DOCUMENTS

| | | | | |
|---|---|---|---|---|
| 5,148,812 A | * | 9/1992 | Verrier | A61B 5/35 600/517 |
| 5,391,199 A | | 2/1995 | Ben Haim | |
| 5,840,038 A | * | 11/1998 | Xue | A61B 5/349 600/512 |

(Continued)

FOREIGN PATENT DOCUMENTS

| | | |
|---|---|---|
| EP | 1510172 A2 | 3/2005 |
| WO | WO1996005768 A1 | 2/1996 |
| WO | WO2001076461 A2 | 10/2001 |

*Primary Examiner* — Oommen Jacob

(57) ABSTRACT

Medical apparatus includes a probe configured for insertion into a chamber of a heart of a patient and including one or more intracardiac electrodes. Interface circuitry acquires intracardiac electrogram signals from the intracardiac electrodes and electrocardiogram (ECG) signals from body-surface electrodes that are fixed to a body surface of the patient. A processor detects, in each of the heartbeats in the sequence, a P wave in the acquired ECG signals and identifies one or more of the heartbeats in the sequence as ectopic beats responsively to a morphology of the detected P wave in the heartbeats. The processor extracts electrophysiological parameters from the intracardiac electrogram signals acquired during the sequence of the heartbeats and generates a map of the extracted electrophysiological parameters while excluding from the map the intracardiac electrogram signals that were received during the ectopic beats.

16 Claims, 2 Drawing Sheets

(56) References Cited

U.S. PATENT DOCUMENTS

| | | | |
|---|---|---|---|
| 6,167,303 A * | 12/2000 | Thompson | A61N 1/378 607/2 |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |
| 6,944,495 B2 * | 9/2005 | MacAdam | A61B 5/364 600/521 |
| 7,139,604 B1 * | 11/2006 | Mouchawar | A61N 1/3621 607/9 |
| 2001/0056289 A1 * | 12/2001 | Sippensgroenewegen | A61B 5/743 607/5 |
| 2002/0038093 A1 * | 3/2002 | Potse | A61B 5/364 600/513 |
| 2002/0065455 A1 | 5/2002 | Ben Haim | |
| 2002/0123769 A1 * | 9/2002 | Panken | A61N 1/368 607/9 |
| 2003/0120150 A1 | 6/2003 | Govari | |
| 2004/0068178 A1 | 4/2004 | Govari | |
| 2004/0127805 A1 * | 7/2004 | MacAdam | A61B 5/283 600/515 |
| 2005/0182336 A1 * | 8/2005 | Sippens Groenewegen | A61B 5/6831 600/518 |
| 2007/0106287 A1 * | 5/2007 | O'Sullivan | A61B 18/1492 607/9 |
| 2008/0167567 A1 * | 7/2008 | Bashour | A61B 5/352 600/521 |
| 2009/0099468 A1 * | 4/2009 | Thiagalingam | A61B 5/349 600/515 |
| 2012/0184858 A1 * | 7/2012 | Harlev | A61B 5/283 600/509 |
| 2014/0128758 A1 * | 5/2014 | Galloway | A61B 5/02438 600/521 |
| 2015/0190068 A1 * | 7/2015 | Cole | A61B 5/349 600/509 |
| 2015/0313480 A1 * | 11/2015 | Razavi | G16H 20/10 702/19 |
| 2016/0213270 A1 * | 7/2016 | Cao | A61N 1/3987 |
| 2016/0213275 A1 * | 7/2016 | Cao | A61B 5/4836 |
| 2016/0325101 A1 * | 11/2016 | Rosenberg | A61B 5/0295 |
| 2018/0008203 A1 | 1/2018 | Iyun | |
| 2019/0223808 A1 | 7/2019 | Rubinstein | |
| 2021/0186351 A1 * | 6/2021 | Govari | A61B 5/35 |

* cited by examiner

HANDLING ECTOPIC BEATS IN ELECTRO-ANATOMICAL MAPPING OF THE HEART

CROSS-REFERENCE TO RELATED APPLICATION

This application is a continuing application of U.S. application Ser. No. 16/724,706, filed Dec. 23, 2019.

FIELD OF THE INVENTION

The present invention relates generally to invasive medical diagnostic systems and methods, and particularly to electro-anatomical mapping of the heart.

BACKGROUND

An electro-anatomical map of a chamber of the heart shows both the physical structure of the wall of the heart chamber and the distribution of electrophysiological parameters, such as the local activation time (LAT), over the wall. The LAT is the time interval between a reference time determined, for example, from the body surface ECG or intracardiac electrogram, and the time of the local depolarization event in the heart wall. The electro-anatomical map is typically based on intracardiac electrical measurements made by a suitable transvascular catheter. A number of systems for electro-anatomical mapping are commercially available, such as the Carto® system produced by Biosense Webster Inc. (Irvine, California).

In some diagnostic procedures, intracardiac electrical measurements are combined with simultaneous body-surface measures of electrocardiogram (ECG) signals. For example, U.S. Patent Application Publication 2019/0223808, whose disclosure is incorporated herein by reference in its entirety as though set forth in full, describes a method for heartbeat classification based on time sequence and morphology of intracardiac (IC) and body surface (BS) ECG signals. The IC-ECG signals are discriminated as atrial (A–) activity or ventricular (V–) activity, and IC annotations are designated as IC-A annotations or IC-V annotations, respectively. A respective A/V time sequence comparison of IC annotations reflective of the sensed heartbeat is made with one or more time sequence templates for heartbeat classification. Morphology comparisons of the BS-ECG oscillating signal segments reflective of the sensed heartbeat morphology templates for classification may also be made.

As noted in the above publication, morphology of the ECG can be a useful tool in classification of heartbeats and identification of arrhythmias. In this regard, U.S. Patent Application Publication 2018/0008203, whose disclosure is incorporated herein by reference in its entirety as though set forth in full, describes methods in which beats are classified automatically according to a resemblance of the morphologic characteristics of the beats to members of a set of templates. FIGS. 4 and 5 in this publication show a morphology matching filter that may be used in such classifications, while FIGS. 6 and 7 show specific algorithms for implementation of morphological correlation in such a filter. These morphological filters and associated computations are described in detail in paragraphs 0058-0070 of the publication.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered. Specifically, the terms "electrocardiogram" and "ECG," as used in the description that follows and in the claims, refers to electrical signals acquired from skin electrodes on the body surface, whereas the term "intracardiac electrogram" refers to electrical signals acquired by a probe within the heart. The term "morphology" is used in the present description and in the claims to refer to shape characteristics of the ECG, including amplitudes, widths and contours of the waves making up the ECG signal.

SUMMARY

Exemplary embodiments of the present invention that are described hereinbelow provide improved methods and systems for electro-anatomical mapping.

There is therefore provided, in accordance with an exemplary embodiment of the invention, medical apparatus, including a probe configured for insertion into a chamber of a heart of a patient and including one or more intracardiac electrodes configured to sense electrical potentials in tissue in the chamber during a sequence of heartbeats. Interface circuitry is configured to acquire intracardiac electrogram signals from the one or more intracardiac electrodes and to acquire electrocardiogram (ECG) signals from body-surface electrodes that are fixed to a body surface of the patient. A processor is configured to detect, in each of the heartbeats in the sequence, a P wave in the acquired ECG signals and to identify one or more of the heartbeats in the sequence as ectopic beats responsively to a morphology of the detected P wave in the one or more of the heartbeats, and to extract electrophysiological parameters from the intracardiac electrogram signals acquired during the sequence of the heartbeats and to generate a map of the extracted electrophysiological parameters while excluding from the map the intracardiac electrogram signals that were received during the ectopic beats.

In one exemplary embodiment, the electrophysiological parameters include local activation times (LATs) extracted from the intracardiac electrogram signals acquired from multiple locations in the chamber of the heart.

In a disclosed exemplary embodiment, the apparatus includes a position-tracking subsystem, which is configured to acquire position coordinates of the probe in the chamber, wherein the processor is configured to apply the position coordinates in generating the map.

In some exemplary embodiments, the probe is configured for insertion into an atrium of the heart, and the processor is configured to map the extracted electrophysiological parameters over the atrium while identifying and excluding from the map the ectopic beats that occurred due to premature atrial contractions. Typically, the processor is configured to identify and exclude the ectopic beats that occurred due to premature atrial contractions from the map even when an RR interval of the ectopic beats does not differ significantly from preceding heartbeats in the sequence.

In a disclosed exemplary embodiment, the processor is configured to create a template of the P wave based on a series of the acquired ECG signals, and to identify the ectopic beats by comparing the ECG signals to the template.

There is also provided, in accordance with an exemplary embodiment of the present invention, a method for electrophysiological measurement, which includes acquiring intracardiac electrogram signals from tissue in a chamber of a heart of a patient during a sequence of heartbeats, and acquiring electrocardiogram (ECG) signals during the sequence of heartbeats from body-surface electrodes that are fixed to a body surface of the patient. In each of the heartbeats in the sequence, a P wave is detected in the digitized ECG signals, and one or more of the heartbeats in the sequence are identified as ectopic beats responsively to a morphology of the detected P wave in the one or more of the heartbeats. Electrophysiological parameters are extracted from the intracardiac electrogram signals acquired during the sequence of the heartbeats, and a map of the extracted electrophysiological parameters is generated while excluding from the map the intracardiac electrogram signals that were received during the ectopic beats.

BRIEF DESCRIPTION OF THE DRAWINGS

The present invention will be more fully understood from the following detailed description of the embodiments thereof, taken together with the drawings in which.

DETAILED DESCRIPTION OF EXEMPLARY EMBODIMENTS

Figure 1:
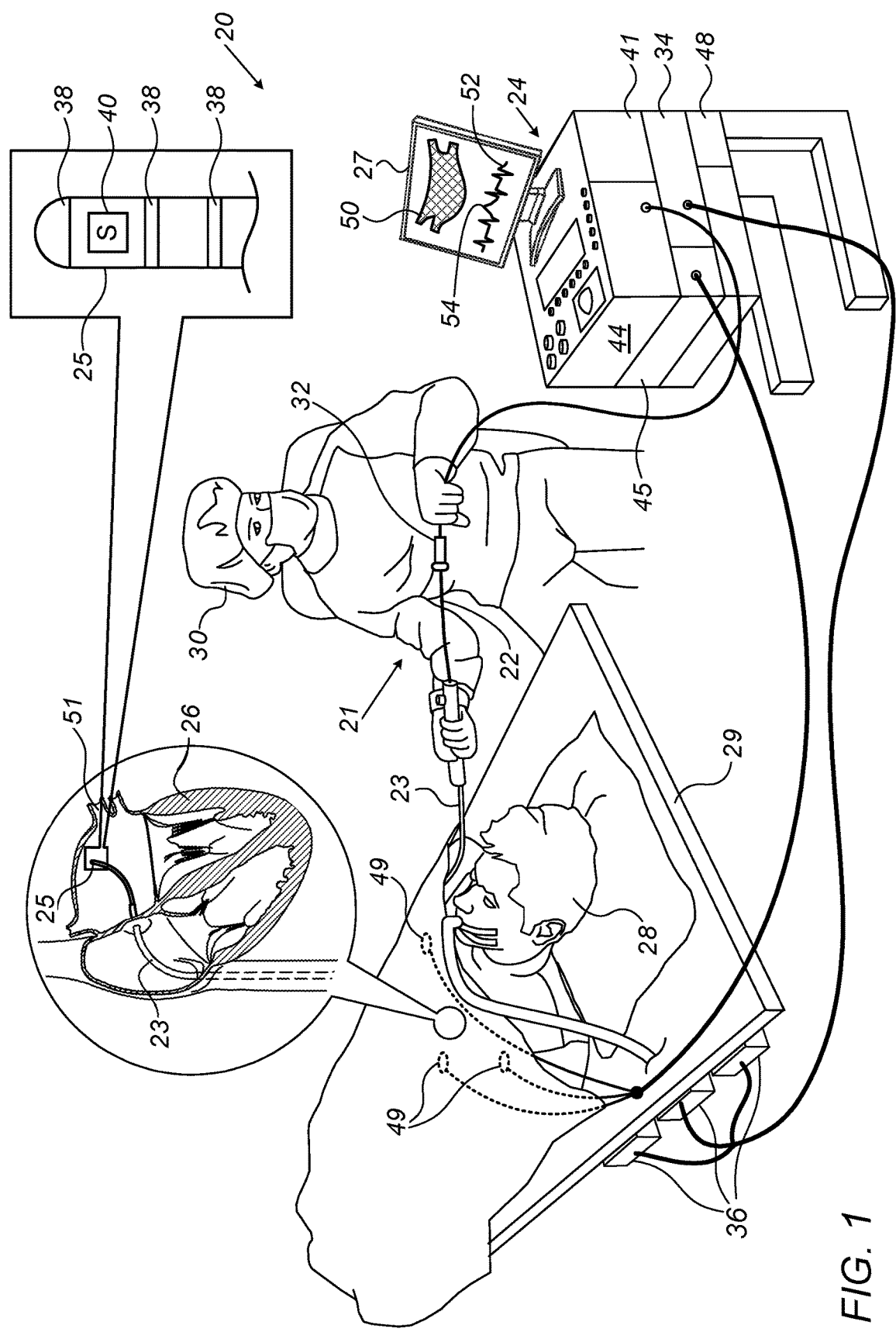
FIG. 1 is a schematic, pictorial illustration of a system for electrophysiological measurement and mapping of the heart, in accordance with an exemplary embodiment of the present invention.

The P wave in the ECG generally occurs in each heartbeat due to atrial depolarization, which results in atrial contraction. Normally, the depolarization front in the heart starts from the sinoatrial node in the right atrium, and then travels through the left atrium to the ventricles. Depolarization of the ventricles gives rise to the QRS complex in the ECG, which normally occurs after a short delay following the P wave.

Abnormal conduction in the atria, however, can sometimes give rise to atrial ectopic beats, in which there is a loss of synchronization between the atrial and ventricular contractions. Atrial ectopic beats are associated with a premature atrial complex in the ECG, which can be recognized on the basis of corresponding changes in the morphology of the P wave. Notwithstanding the premature atrial complex, the P wave in an atrial ectopic beat is commonly followed by a normal QRS complex, and the RR interval (i.e., the heartbeat duration) of an occasional atrial ectopic beat may not differ significantly from preceding heartbeats in the sequence. The term "significant" is used in the present description and in the claims in the statistical sense, to denote differences that are outside the expected bounds of random variation; for example, the RR interval of a heartbeat can be considered to be significantly different from a preceding sequence of heartbeats if it differs from the mean RR interval of the preceding sequence by more than twice the standard deviation of the RR intervals in the preceding sequence, or by more than a given fraction, such as 10%, of the mean.

In electro-anatomical mapping, as performed in the above-mentioned Carto system, for example, intracardiac electrograms are acquired from multiple locations within a chamber of the heart over a period of many heartbeats. When temporal characteristics, such as the LAT, are to be mapped, the electrogram signals that are acquired over multiple heartbeats are commonly synchronized with one another using a reference point in the ECG, such as the peak of the R wave. When ectopic beats occur during electro-anatomical mapping of a heart chamber, however, the synchronization of the electrogram signals with the reference point is lost; and incorporation of the signals acquired during ectopic beats can thus introduce noise and errors into the map. For this reason, when an electro-anatomical mapping system detects that the RR interval of a given heartbeat differed significantly from that of the sequence of heartbeats preceding it, the system will commonly discard the electrogram signals acquired during the given heartbeat.

In atrial ectopic beats, however, the RR interval in many cases does not differ significantly from that of the preceding heartbeats. The abnormal atrial conduction that occurs during such heartbeats can introduce errors into electro-anatomical maps of the atria, and filtering out heartbeats on the basis of the RR interval alone will not eliminate this source of error.

To alleviate this problem, exemplary embodiments of the present invention that are described herein identify changes in the morphology of the P wave, as acquired by the body-surface electrodes in the ECG signal. When some aspect of the P wave morphology in a given heartbeat differs significantly from the P waves in the preceding sequence of heartbeats, the atrial electrogram signals acquired in the given heartbeat are excluded from the map.

Thus, the disclosed exemplary embodiments provide medical apparatus and diagnostic methods in which a probe, such as a catheter, is inserted into a chamber of the heart of a patient, such as one of the atria. Intracardiac electrodes on the probe sense electrical potentials in the myocardial tissue in the chamber during a sequence of heartbeats. Interface circuitry, such as an analog front end and digitization circuits, acquires intracardiac electrogram signals from the intracardiac electrodes and simultaneously acquires ECG signals from body-surface electrodes that are fixed to the body surface of the patient.

A processor detects a P wave in the acquired ECG signals in each of the heartbeats, and identifies ectopic beats based on the morphology of the detected P waves. The processor also extracts electrophysiological parameters, such as the LAT, from the intracardiac electrogram signals acquired during the sequence of the heartbeats, and generates a map incorporating these parameters, while excluding from the map the intracardiac electrogram signals that were received during the identified ectopic beats. Specifically, the processor may exclude in this manner ectopic beats that occurred due to premature atrial contractions, even when the RR intervals of the ectopic beats did not differ significantly from preceding heartbeats in the sequence.

FIG. 1 is a schematic, pictorial illustration of a catheter-based system 20 for electrophysiological (EP) sensing and mapping of the heart, in accordance with an exemplary embodiment of the present invention. System 20 comprises a catheter 21, comprising an insertion tube 22 for transvascular insertion into a heart 26 of a patient 28, who is shown lying on a table 29. A distal end 25 of insertion tube 22 (as seen in the inset in FIG. 1) includes one or more electrodes 38, which contact and sense electrical potentials in the myocardial tissue in heart 26. Although distal end 25 is shown in FIG. 1, for the sake of simplicity, as a single linear structure, in alternative embodiments, the distal end of catheter 21 may have other features and shapes that are known in the art, such as multiple arms or a basket configuration, for example. Distal end 25 also contains a magnetic position sensor 40, whose functionality is described further hereinbelow.

The proximal end of catheter 21 is connected to catheter interface circuitry 44 in a control console 24. Interface circuitry 44 typically comprises an analog front end, including suitable amplifiers and filters for acquiring intracardiac electrogram signals from electrodes 38, and one or more analog/digital converters for converting the signals to digital samples. In addition ECG interface circuitry 45 in console 24 receives, amplifies, filters and digitizes ECG signals from body-surface electrodes 49 that are fixed to the body surface of patient 28. The digital samples from interface circuitry 44, 45 are input to a processor 41 in console 24.

To carry out a diagnostic mapping procedure, a physician 30 first inserts a sheath 23 into heart 26 of patient 28, and then passes insertion tube 22 through the sheath. Physician 30 advances distal end 25 of insertion tube 22 toward a target location in heart 26, for example within a left atrium 51 of the heart, by manipulating catheter 21 using a manipulator 32 near the proximal end of the catheter. Once distal end 25 of insertion tube 22 has reached the left atrium in heart 26, physician 30 retracts sheath 23 and manipulates catheter 21 so that electrodes 38 contact the myocardial tissue at multiple locations. Console 24 may verify that the electrodes are in good contact with the tissue by measuring the impedance between each of the electrodes and the tissue.

During this procedure, a position-tracking subsystem in system 20 applies magnetic position sensing in tracking the location and orientation of distal end 25 of insertion tube 22 within heart 26. For this purpose, as shown in the inset in FIG. 1, distal end 25 of insertion tube 22 contains magnetic position sensor 40, comprising a miniature wire coil or multiple coils, for example. One or more magnetic field generators 36 are fixed in known positions in proximity to the body of patient 28, for example under bed 29 as shown in FIG. 1. A driver circuit 34 in console 24 applies drive signals to the magnetic field generators so as to produce multiple magnetic field components directed along different, respective axes. During navigation of distal end 25 in heart 26, magnetic sensor 40 outputs electrical signals in response to the magnetic field components. Position sensing circuitry, such as processor 41 in console 24, receives these signals via interface circuits 44, and processes the signals in order to find the position (location and orientation) coordinates of distal end 25. These coordinates also indicate the respective locations of electrodes 38.

The methods and apparatus for magnetic position sensing that are implemented in system 20 are based on those that are used in the above-mentioned Carto system. The principles of operation of this sort of magnetic sensing are described in detail, for example, in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all hereby incorporated by reference herein in their entireties as though set forth in full.

Alternatively or additionally, system 20 may implement other position sensing technologies that are known in the art, including both magnetic sensing modalities and other position sensing techniques. For example, processor 41 may measure and analyze electrical impedances between intracardiac electrodes 38 and body-surface electrodes 49 in order to find the location coordinates of the intracardiac electrodes.

In some exemplary embodiments, processor 41 comprises a general-purpose computer, with suitable interface circuits 44, 45 for receiving signals from catheter 21 and body-surface electrodes 49 (including low-noise amplifiers and analog/digital converters), as well as for receiving signals from and controlling the operation of the other components of system 20. Processor 41 typically performs these functions under the control of software stored in a memory 48 of system 20. The software may be downloaded to the computer in electronic form, over a network, for example, or it may, alternatively or additionally, be provided and/or stored on non-transitory tangible media, such as magnetic, optical, or electronic memory. Additionally or alternatively, at least some of the functions of processor 41 may be carried out by dedicated or programmable hardware logic.

Based on the intracardiac electrogram signals acquired from electrodes over a sequence of heartbeats, processor generates an electro-anatomical map 50 and, in the pictured example, renders the map to a display 27. Map 50 includes the electrophysiological parameters extracted at each point in the heart chamber (such as in left atrium 51), such as the LAT or peak voltage measured at each point. The parameter values may be superimposed on the map, for example, as numerical values or as corresponding color coding.

As noted above, processor 41 also acquires an ECG signal 52 from body-surface electrodes (and in the pictured example, presents the ECG signal on display 27, as well). Processor 41 detect a P wave 54 in each of the heartbeats in the acquired ECG signals and analyzes the morphology of the P wave in order to identify ectopic beats. In generating map 50, processor 41 excludes the intracardiac electrogram signals that were acquired from electrodes 38 during the ectopic beats.

Figure 2:
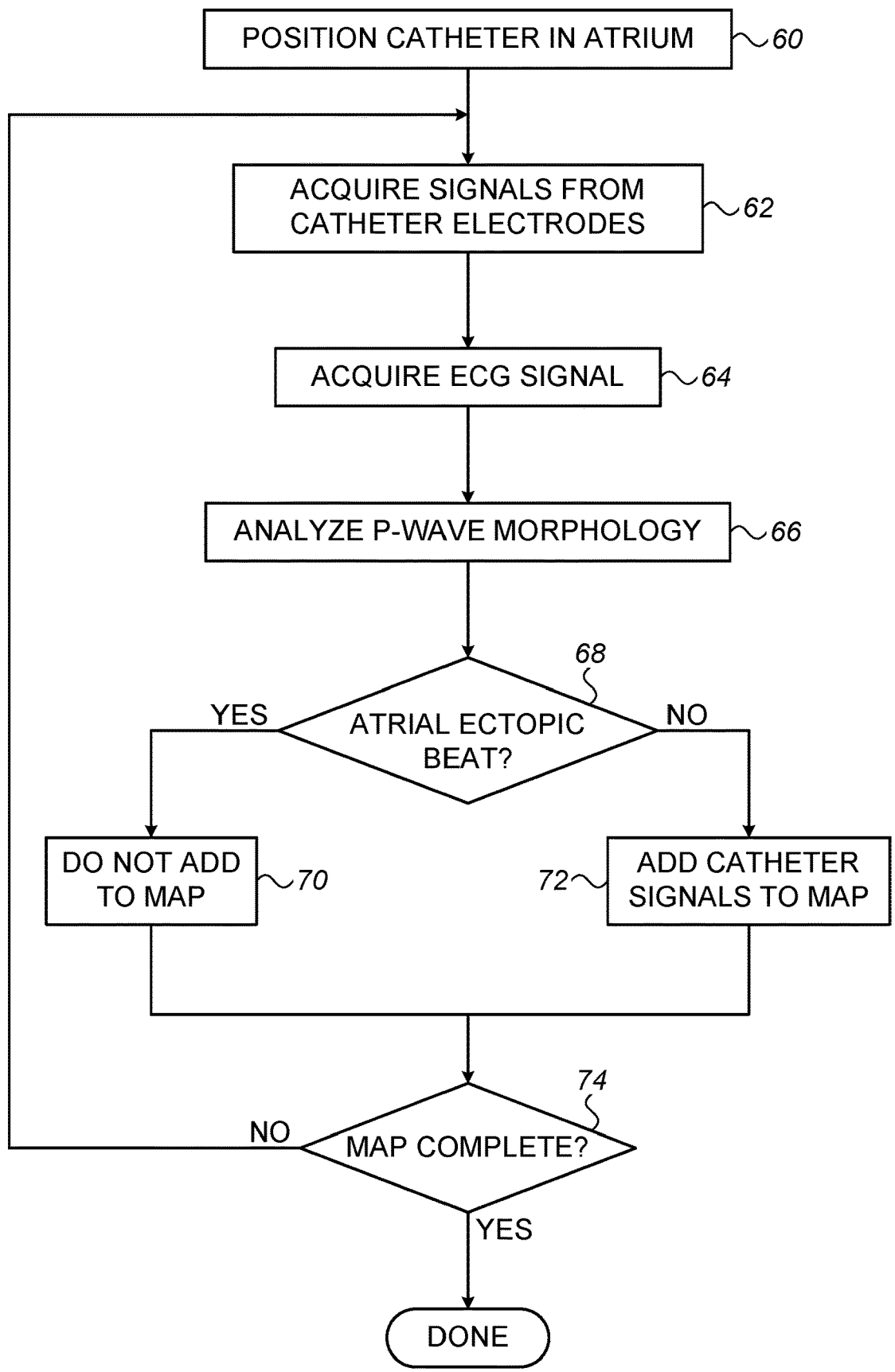
FIG. 2 is a flow chart that schematically illustrates a method for electro-anatomical mapping of the heart, in accordance with an exemplary embodiment of the invention.

FIG. 2 is a flow chart that schematically illustrates a method for electro-anatomical mapping of the heart, in accordance with an exemplary embodiment of the invention. The method is described hereinbelow, for the sake of clarity and concreteness, with reference to the elements of system 20, as shown in FIG. 1. Alternatively, the principles of this method map be applied, mutatis mutandis, in other sorts of electro-anatomical mapping configurations.

Physician 30 advances catheter 21 through the vascular system of patient 28 until distal end 25 is positioned in atrium 51 of heart 26, at a probe positioning step 60. Processor 41 acquires intracardiac electrogram signals from electrodes 38 on distal end 25 via catheter interface circuitry 44, at an electrogram acquisition step 62. Processor 41 simultaneously acquires ECG signals from body-surface electrodes 49 via ECG interface circuitry 45, at an ECG acquisition step 64.

Processor 41 analyzes the morphology of the ECG signals, and specifically the morphology of the P wave in each heartbeat, at a morphology analysis step 66. For example, processor 41 may create a template of the P wave by averaging the ECG signals over a certain number of heartbeats in which the ECG signal was stable, and may then compute a correlation between subsequent heartbeats and this template. The template creation and subsequent correlation may be performed over any or all of the signals from the various ECG leads; but these operations are most advantageously applied to the signals from leads II and V1, in which the P wave is usually most prominent.

In one exemplary embodiment, for the purposes of step 66, an operator, such as physician 30, identifies a time window in which the P wave occurs in a series of heartbeats. The time window can be defined relative to an annotation point, such as the R wave peak in the ECG signal. Processor 41 accumulates the ECG signals over an initial reference period and verifies that they have the expected overall shape (typically a shallow hump, in the case of the P wave) and are consistent from beat to beat, for example with signal/noise ratio above a predefined minimum level and variance among beats below a maximum limit. Processor 41 combines the accumulated signals, for example by averaging the signals, to create a template, which then serves as a kernel for comparison of subsequent heartbeats. The comparison may be carried out, for example, by computing a cross-correlation between the kernel and the portion of the ECG signal falling within the P wave time window that was defined by the operator. Alternatively or additionally, processor 41 may apply a certain transformation to the template and to the subsequent signals, such as a Fourier transform, wavelet transform, or multipole transform, for example, and may then compare the transform coefficients at step 66.

Further alternatively or additionally, other sorts of morphological computations may be applied to the ECG signals, such as those described in the above-mentioned U.S. Patent Application Publication 2018/0008203. Processor 41 may test and apply not only the morphology of the P wave in deciding which signals to include and which to exclude from the electro-anatomical map, but also other features of the ECG signals.#

Processor 41 checks the results of the morphological analysis in order to classify the current heartbeat as either normal or ectopic, at a classification step 68. When the correlation of the P wave in a given heartbeat with the morphological template drops significantly below a certain baseline correlation level, for example, processor 41 identifies the given heartbeat as an ectopic beat. In this case, the intracardiac electrogram signals acquired during the given heartbeat are excluded from the map, at a map exclusion step 70. Processor 41 will identify and exclude ectopic beats of this sort, which evidently occurred due to premature atrial contractions, even when the RR interval of the ectopic beats did not differ significantly from preceding heartbeats in the sequence. (In addition, processor 41 will generally exclude from the map heartbeats in which the RR interval differed significantly from preceding heartbeats or that manifested other anomalous features, regardless of P wave morphology.) The excluded data may be discarded or, alternatively, processor 41 may incorporate the excluded data into another map or other report regarding the heart's arrhythmic behavior.

On the other hand, when the ECG signal in a given heartbeat was found to have a normal morphology at step 68, processor 41, derives the electrophysiological parameters on interest from the intracardiac electrogram signals, and incorporates the parameters into the map, at a map addition step 72.

After updating the electro-anatomical map as appropriate, processor 41 decides whether the map includes sufficient data, at a map completion step 74. (The decision may be made, for example, in response to a corresponding input from physician 30.) If so, the process of FIG. 2 terminates. Otherwise, processor 41 returns to step 62 and repeats the cycle of acquisition, analysis and mapping.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A non-transitory computer readable storage medium having stored thereon instructions that, when executed, cause a processor of a device to:
   generate a P wave template based on ECG signals of the patient acquired over an initial reference period, wherein the reference period includes a plurality of heartbeats and wherein the P wave template is defined as the average of a set of P waves detected over the initial reference period;
   store the P wave template in memory;
   receive subsequent electrocardiogram (ECG) signals acquired from body-surface electrodes fixed to a body surface of a patient;
   receive intracardiac electrogram signals acquired from the one or more intracardiac electrodes in a heart chamber of the patient, wherein the subsequent ECG signals and the intracardiac electrogram signals are acquired over a same sequence of heartbeats;
   compute values of an electrophysiological parameter from the intracardiac electrogram signals over the sequence of heartbeats;
   detect P waves in the subsequent ECG signals;
   determine a correlation between each of the detected P waves in the subsequent ECG signals and the template stored in memory over the sequence of heartbeats;
   identify one or more of the heartbeats in the sequence as an ectopic beat based on identifying a significant drop in the correlation over the sequence of heartbeats; and
   generate a map of the values while excluding from the map, a portion of the values that were computed from heartbeats identified as an ectopic beat.

2. The non-transitory computer readable storage medium according to claim 1, wherein the electrophysiological parameter is local activation times (LATs) from the intracardiac electrogram signals acquired from multiple locations in the chamber of the heart.

3. The non-transitory computer readable storage medium according to claim 1, wherein the instructions, when executed, further cause the processor to:
   receive position coordinates of the one or more intracardiac electrodes; and
   apply the position coordinates in generating the map.

4. The non-transitory computer readable storage medium according to claim 1, wherein the instructions, when executed, further cause the processor to selectively include in the average of a set of P waves detected over the initial reference period P waves with a signal to noise ratio above a predefined minimum level in the set of P waves.

5. The non-transitory computer readable storage medium according to claim 4, wherein the instructions, when executed, further cause the processor to selectively include in the average of a set of P waves detected over the initial reference period P waves with variance in morphology below a predefined maximum limit in the set of P waves.

6. The non-transitory computer readable storage medium according to claim 1, wherein the instructions, when executed, further cause the processor to selectively include include in the average of a set of P waves detected over the initial reference period P waves with a signal to noise ratio above a predefined minimum level and variance in morphology below a predefined maximum limit in the set of P waves.

7. The non-transitory computer readable storage medium according to claim 1, wherein the instructions, when executed, further cause the processor to compute a cross-correlation between each of the detected P waves in the sequence of heartbeats and the template.

8. The non-transitory computer readable storage medium according to claim 1 wherein the instructions, when executed, further cause the processor to compute a Fourier transform or a wavelet transform of the each of the detected P waves in the sequence of heartbeats and the template and compare the computed transforms.

9. A method for electro-anatomical mapping of the heart, the method comprising:
  generating a P wave template based on ECG signals of the patient acquired over an initial reference period, wherein the reference period includes a plurality of heartbeats and wherein the P wave template is defined as the average of a set of P waves detected over the initial reference period;
  storing the P wave template in memory;
  receiving electrocardiogram (ECG) signals acquired from body-surface electrodes fixed to a body surface of a patient;
  receiving subsequent intracardiac electrogram signals acquired from the one or more intracardiac electrodes in a heart chamber of the patient, wherein the ECG signals and the intracardiac electrogram signals are acquired over a same sequence of heartbeats;
  computing values of an electrophysiological parameter from the intracardiac electrogram signals over the sequence of heartbeats;
  detecting P waves in the subsequent ECG signals;
  determining a correlation between each of the detected P waves in the subsequent ECG signals and a template stored in memory over the sequence of heartbeats;
  identifying one or more of the heartbeats in the sequence as an ectopic beat based on identifying a significant drop in the correlation over the sequence of heartbeats; and
  generating a map of the values while excluding from the map, a portion of the values that were computed from heartbeats identified as an ectopic beat.

10. The method according to claim 9, wherein the electrophysiological parameter is local activation times (LATs) from the intracardiac electrogram signals acquired from multiple locations in the chamber of the heart.

11. The method according to claim 9, further comprising:
  receiving position coordinates of the one or more intracardiac electrodes; and
  applying the position coordinates in generating the map.

12. The method according to claim 9, further comprising selectively including in the average of a set of P waves detected over the initial reference period P waves with a signal to noise ratio above a predefined minimum level in the set of P waves.

13. The method according to claim 9, further comprising selectively including in the average of a set of P waves detected over the initial reference period P waves with variance in morphology below a predefined maximum limit in the set of P waves.

14. The method according to claim 9, further comprising selectively including in the average of a set of P waves detected over the initial reference period P waves with a signal to noise ratio above a predefined minimum level and variance in morphology below a predefined maximum limit in the set of P waves.

15. The method according to claim 9, further comprising computing a cross-correlation between each of the detected P waves in the sequence of heartbeats and the template.

16. The method according to claim 9, further comprising computing a Fourier transform or a wavelet transform of the each of the detected P waves in the sequence of heartbeats and the template and comparing the computed transforms.

* * * * *